United States Patent [19]

Harley

[11] Patent Number: 5,264,351
[45] Date of Patent: Nov. 23, 1993

[54] MONOCLONAL ANTIBODIES AGAINST AUTOIMMUNE RNA PROTEINS

[75] Inventor: John B. Harley, Oklahoma City, Okla.

[73] Assignee: The Board of Regents For The University of Oklahoma, Norman, Okla.

[21] Appl. No.: 269,983

[22] Filed: Nov. 9, 1988

Related U.S. Application Data

[63] Continuation of Ser. No. 670,000, Nov. 5, 1984, Pat. No. 4,784,942.

[51] Int. Cl.$^5$ .............................................. C07K 15/28
[52] U.S. Cl. .............................. 435/70.21; 530/388.2; 530/868; 435/240.27
[58] Field of Search ............... 435/68, 240.27, 172.2, 435/70.21; 530/387, 388, 808, 809, 388.2, 868

[56] References Cited

U.S. PATENT DOCUMENTS 3,654,090  4/1972  Hermanus ...................... 195/103.5
4,564,597  1/1986  Lerner et al. ......................... 435/7

OTHER PUBLICATIONS

Lerner et al., Science 211 (Jan. 23, 1981) 400–2.
Kahler et al., Nature, vol. 256, pp. 495–497 (1975).
Eilat et al., J. of Immunology, vol. 124 No. 2, pp. 766–768 (1980).
Pisetsky et al., J. of Immunology, vol. 129 No. 4, pp. 1489–1492 (1982).
Yamagata et al., "Molecular Properties of the Ro/SSA Antigen and ELISA for Quantitation of Antibody", J. Clin. Invest., vol. 74, pp. 625–633 (1984).
Abstract, Williams et al., "Use of Monoclonal Anti-La Antibodies to Study the Concentration and Distribution of La in Normal and Transformed Cells", 609th Meeting, Biochemical Socieity, Jul. 18–20, 1984, p. 46.
Meeting, Biochemical Society, Jul. 18–20, 1984, p. 46.
Abstract, Smith et al., "Production of Monoclonal Antibodies to La Antigen", 609th Meeting, Biochem. Soc., Jul. 18–20, 1984, p. 46.
Harley et al., "Anti-La/SSB Antibody is Present in Some Normal Sera and is Coincident with Anti--Ro/SSA Precipitins in Systemic Lupus Erythematosus", J. Rheumatol., vol. 11, No. 3, (1984), pp. 309–314 (1984).
Abstract A1, Lieu, "Isolation of SS-B/la Antigen Reacting with Antibodies in the Sera of Patients with Sjogren's Syndrome and Systemic Lupus Erythematosus", 48th Ann. Meeting, Am. Rheu. Assn/19th Ann. Meet., Arthritis Health Professions Assn, Jun. 5–9, 1984, p. S42.
Abs. A3, Harley et al., "The Molecular Structure of Ro/SSA", 48th Ann. Meet., Am. Rheu.Assn/19 Ann. Meet., Jun. 5–9, 1984, p. S42.
Abs. A27, Harley et al., "Relationships of Rel. Quantitative Levels of Anti-Ro/SSA,-LaSSB AND -nRNP (Sm) to Clin. Manifestations of Sjogren's Syndrome", 609th Ann. Meet, Biochem. Soc., Jul. 18–20, 1984, p. S46.
Abs. D46, Rader et al., "The Capacity of Anti-La/SSB Autoantibody Found in SLE Patients and Normal Donors to Activate Complement", 609th Meet., Biochem. Soc., Jul. 18–20, 1984, p. S83.

(List continued on next page.)

Primary Examiner—Christine M. Nucker
Attorney, Agent, or Firm—Dunlap, Codding & Lee

[57] ABSTRACT

Monoclonal antibodies against autoimmune RNA proteins such as La/SSB, Ro/SSA, nNP and Sm. These monoclonal antibodies, which are produced by a continuous hybridoma cell line, may be used in methods for detecting the presence of selected autoimmune RNA proteins and antibodies against such proteins in biological samples, and may be incorporated into diagnostic test kits for this purpose. The monoclonal antibodies may be applied in methods for screening subjects for systemic lupus erythematosus, subacute cutaneous erythematosus, neonatal lupus, Siögren's syndrome, complete congential heart block, and other disorders which involve the presence of antibodies against autoimmune RNA proteins.

28 Claims, No Drawings

OTHER PUBLICATIONS

Abs., Harley et al., "Complement Activation by the Anti–La/SSB Auto Antibody Found in SLE Patients & Normal Donors", Clin. Res., vol. 32, #2, 1984, p. 464A.

Abs., Harley et al., "The Molecular Structure of Ro/SSA", *Clin. Res.*, vol. 2, No. 2, (1984), p. 566A.

Abs., Harley et al., "Some Healthy individuals Make Anti–La/SSB Autoantibodies", Clin. Res., vol. 31, No. 4, (1983), p. 803A.

Abs., Harley et al., "Sjogren's Syndrome (SS), Quantitative Anti Ro/SSA, La/SSB and -nRNP (Sm)", Clin. Res., vol. 32, No. 2, (1984), p. 538A.

Abs., Yamagata et al., "Molecular Structure of Ro/SSA Assay for Anti–Ro/SSA", Clin. Res., vol. 31, No. 4, (1983), p. 808A.

Abs., Harley et al., "Anti–La(SS–B) Commonly Occurs with Anti–Ro(SS–A) in SLE", 47th Ann. Meet., Am. Rheu. Assn.,/18th Ann. Meet, Arthritis Health Professions Assn, Jun. 1–4, 1983, p. S74.

Venables et al., "Quantitation and Detection of Isotypes of Anti SS B Antibodies by ELISA and Farr Assays Using Affinity Purified Antigens", *Arthritis and Rheumatism*, vol. 26, No. 2, (1983), pp. 146–155.

Teppo, "Enzyme Immunoassay of Antibodies to Sjogren's Syndrome B Antigen", *Clin. Chem.*, vol. 27, No. 8, (1981), pp. 1341–1345.

Webster's New Collegiate Dictionary (1979).

Gellrich, "Enzyme Immunoassays in Clinical Chemistry: Present Status and Trends," J. Clin. Chem. Clin. Biochem., 18, 197–208 (1980).

Nusbaum et al., "Monoclonal Antibodies Directed Against the Biologically Active Reagent of Human Parathyroid Hormone," *Clinical Research*, vol. 28, 648A (1980).

Novick et al., "Monoclonal Antibodies to Human 1–Interferon and Their Use for Affinity Chromatography," *Journal of Immunology*, vol. 129, 2244–2247 (1982).

Chang et al., "Development and Characterization of a Monoclonal Anti–SSA/Ro Antibody," *Clinical Research*, vol. 32, 575A (1984).

Williams et al., "Anti–Sm and Anti–La Murine Monoclonal Antibodies: Characterization of the Antigens", *Protides of the Biological Fluids* (1985) at 187–190.

Harley, "Autoantibodies in Sjogren's Syndrome," *Sjogren's Syndrome: Clinical and Immunological Aspects* (Springer Verlag 1986).

Bachmann et al., *Proc. Natl. Acad. Sci. USA*, vol. 83, pp. 7770–7774 (1986).

MONOCLONAL ANTIBODIES AGAINST AUTOIMMUNE RNA PROTEINS

This is a continuation of U.S. patent application Ser. No. 670,000, filed Nov. 5, 1984, now U.S. Pat. No. 4,784,942, which is incorporated by reference.

FIELD OF THE INVENTION

The present invention relates generally to monoclonal antibodies against autoimmune RNA proteins and to immunological and diagnostic testing methods involving the use of such monoclonal antibodies.

SUMMARY OF THE INVENTION

The present invention comprises monoclonal antibodies against an autoimmune RNA protein. These antibodies are generated by a continuous hydridoma cell line which is produced by fusing a myeloma cell with a cell capable of producing antibodies against the autoimmune RNA protein.

The monoclonal antibodies may be used to detect the presence of autoimmune RNA protein in a biological sample by assaying for antibody-RNA protein reaction product in the sample. The monoclonal antibodies of the present invention may also be used to detect the presence of antibodies to the autoimmune RNA protein in a biological sample, and so may be used to screen for systemic lupus erythematosus, subacute cutaneous lupus erythematosus, Sjögren's syndrome, congenital complete heart block and other disorders involving the presence of antibodies to autoimmune RNA protein. In order to detect the presence of antibodies in a sample, the monoclonal antibodies are first treated with a stoichiometric excess of autoimmune RNA protein. The treated monoclonal antibodies are then contacted with the sample. Presence of antibodies in the sample is detected by assaying for antibody-RNA protein reaction which occurs after contacting the sample with the treated monoclonal antibodies.

The present invention further comprises a kit for use in assaying for antibodies against an autoimmune RNA protein comprising a first medium comprising the monoclonal antibodies of the present invention, a second medium comprising animal extract containing a stoichiometric excess of autoimmune RNA protein, and a third medium comprising an enzyme-labelled immunological conjugate to antibodies against the autoimmune RNA protein.

DESCRIPTION OF THE PREFERRED EMBODIMENTS

The present invention is directed to monoclonal antibodies against autoimmune RNA proteins and to methods of preparing and using such monoclonal antibodies. Such autoimmune RNA proteins include La/SSB, Ro/SSA, nRNP and Sm. Antibodies against these proteins are known to occur at high levels in many patients suffering from autoimmune disorders such as systemic lupus erythematosus (SLE) and Sjögren's syndrome. The monoclonal antibodies of the present invention offer an economical and efficient means for diagnosing and screening for these autoimmune disorders.

Purification of Selected Autoimmune RNA Protein

In accordance with the present invention, monoclonal antibodies are prepared against a selected autoimmune RNA Protein. While any of the above-identified RNA proteins may be selected, one RNA protein is La/SSB. When the RNA protein is La/SSB, one preferred variety is bovine La/SSB.

The first step in producing monoclonal antibodies against the selected autoimmune RNA protein is the purification of the selected autoimmune RNA protein, preferably from a mammal such as a human or bovine animal, and more preferably from the spleen or thymus of such a mammal. If the selected protein is unavailable from off-the-shelf sources, it may be obtained by extraction and separation methods, such as the affinity chromatography methods described by Harley et al. (J. Rheumatol. 11, pp. 309-14 [1984]) and Akizuki et al. (J. Immunol. 119, pp. 932-38 [1977]). In these methods an affinity column containing antibody activity in the selected autoimmune RNA protein is utilized to separate the autoimmune RNA protein from other tissue components. Preferably, the affinity column is formed from CNBr-activated Sepharose 4B which is coupled to the purified IgG fraction from an SLE patient with precipitin to antibodies against the selected autoimmune RNA protein.

To verify that the separated fractions containing the selected autoimmune RNA protein are substantially pure, the fractions are preferably analyzed for contamination. Preferred contamination tests include sodium dodecylsulfate polyacrylamide gel electrophoresis using a silver stain, the Western blot technique, and the enzyme-linked immunoabsorbent assay (ELISA) for antibodies against the selected autoimmune RNA proteins.

If contamination studies reveal that autoimmune RNA proteins, immunoglobulins and other contaminants were separated by the above-described chromatographic procedure, these substances may be removed from the separated fraction containing the selected autoimmune RNA protein, preferably by treating the fraction with a monospecific anti-protein, by performing further anti-human immunoglobulin affinity column procedures, or by using additional physical separation procedures including, but not limited to, gel filtration, ion exchange chromatography, isoelectric focusing, chromatofocusing and adsorption into Staph A Sepharose.

Once the necessary separation steps have been completed, the substantially pure selected autoimmune RNA protein preferably is suspended in a biologically acceptable carrier, preferably 0.02M Tris or 0.02M phosphate and 150 mM NaCl at pH 7.4. The preparation then is preferably cooled, concentrated and stored.

Animal Immunization With Autoimmune RNA Protein

In accordance with the present invention, cells capable of producing antibodies to the selected autoimmune RNA protein are obtained by immunizing an immunoresponsive animal with the purified preparation of the selected autoimmune RNA protein. Preferably, the animal to be immunized is of a different species than the species from which the selected autoimmune RNA protein is extracted, so that immunization will cause the immunized animal to produce heteroantibodies. The animal selected for immunization is preferably a mammal, more preferably a mouse, and, most preferably, a Balb/c mouse.

The animal is immunized with the preparation containing the substantially pure selected autoimmune RNA protein, preferably in combination with an equal amount of an immunological adjuvant, in an amount sufficient to generate production of substantial numbers of cells producing antibodies to the selected autoimmune RNA protein. Preferably, the animal is first injected subcutaneously with purified selected autoimmune RNA protein in an amount sufficient to initiate an immune response in the animal. The initial dosage of protein is preferably administered in combination with an equal amount of an adjuvant, such as Freund's Complete Adjuvant. In a preferred embodiment, 50 μg of purified selected autoimmune RNA protein suspended in between about 50 μl and about 300 μl, and most preferably in about 200 μl of 0.02M phosphate or Tris and 150 mM NaCl at pH 7.4, is administered to the animal by subcutaneous injection as a suspension which also contains 200 μl of Freund's Complete Adjuvant.

Fourteen days after the initial subcutaneous injection, the animal preferably is boosted by intraperitoneal injection of an additional amount of purified selected autoimmune protein, which preferably is administered in combination with an equal amount of an adjuvant, such as Freund's Incomplete Adjuvant. In a preferred embodiment, the first booster injection comprises 10 μg of purified selected autoimmune RNA protein suspended in between about 50 μl to about 250 μl, and more preferably in 200 μl of 0.02M phosphate or Tris and 150 mM NaCl at pH 7.4, and is administered to the animal in combination with 200 μl of Freund's Incomplete Adjuvant.

If required, additional booster injections may be administered to the animal. The number of dosages of such additional boosters will depend upon the animal's response to the immunization and the length of time the animal is to be maintained in an immunized state prior to recovery of antibody-producing cells from the animal. In one preferred embodiment, seven additional booster dosages of selected autoimmune protein are administered to the animal over the four month period following the first booster injection. These seven additional booster dosages preferably comprise between about 10 μg and about 100 μg of selected autoimmune RNA protein suspended in between about 50 μl and about 200 μl, and most preferably 100 μl, of 0.02M phosphate or Tris and 150 mM NaCl at pH 7.4. In this preferred embodiment, the additional booster dosages are administered without adjuvant. Preferably, the last three of such additional booster injections are administered on each of three days before antibody-producing cells are to be recovered from the animal. Each of the additional booster injections preferably is intraperitoneal, except the final injection which most preferably is administered via the tail vein.

Production of Hybridomas

According to the present invention, cells from the animal immunized as described above are fused with a compatible cell line to produce hybridomas capable of producing monoclonal antibodies against the selected autoimmune RNA protein against which the animal was immunized.

Cells producing antibodies to the selected autoimmune RNA protein are recovered from the immunized animal, and preferably from the animal's spleen. The cells are removed under sterile conditions and are prepared for fusion with a compatible myeloma cell line.

Preferably, the myeloma cell line is from the same animal species as the antibody-producing cell, and most preferably, both of the fused cells are murine. A preferred compatible fusion partner cell is the P3 X63-Ag86.5.3 mouse myeloma cell. Preferably, prior to fusion these cells have been suspended in a medium containing hypoxanthine/aminopterin/thymidine (HAT).

The cells recovered from the immunized animal preferably are mixed with the myeloma cells in the presence of a fusion-promoting agent, preferably polyethylene glycol (PEG). Once fusion has occurred between myeloma and antibody-producing cells, the fusion-promoting action preferably is arrested. Preferably, this arresting step is carried out by centrifuging the mixture and removing substantially all the supernatant which results in the removal of substantially all the PEG. The removed supernatant is replaced with either a HAT medium or a modified Dulbecco's minimal essential medium (DMEM).

The fused cells are next cultured in a medium selective for the growth of those hybridoma cells formed by fusing myeloma cells with antibody-producing cells. Preferably, the selective medium comprises HAT and fetal calf serum (FCS). Preferably, the selective culturing is performed by plating out the fused cells onto a 24-well polystyrene macrotiter plate having in each well a selective medium comprising a mixture of HAT and FCS.

The culture supernatant from the wells demonstrating hybridoma growth are screened to determine which of them are producing monoclonal antibodies against the selected autoimmune RNA protein. Preferably, this screening step is carried out by a modified enzyme-linked immunoabsorbent assay (ELISA) using affinity-purified autoimmune RNA protein obtained from the same species of animal as that from which the purified protein preparation used to immunize the animal, as described above, was obtained.

The hybridomas which grow in the selective culture medium are single-cell cloned. Preferably, the cloning is carried out by distributing the hybridomas in the wells of 96-well polystyrene microtiter plates having in each well a nutrient medium. The nutrient medium preferably is the same preparation as that in which the fused cells were suspended and selectively cultured, as described above. Preferably, the nutrient medium also contains fetal bovine serum. More preferably, the fetal bovine serum used is Hybrisure (Hazelton-Dutchland) which was tested to assure it will sustain hybridoma growth. The plates containing the hybridomas in nutrient medium are incubated until the hybridomas have colonized.

After the hybridomas have colonized, as described above, the supernatants are screened, as described above. The cloned cells which are producing antibodies are expanded and used as the source of the monoclonal antibody-producing hybridoma cells.

The above described procedures for fusion, selective hybridoma growth and cloning are adapted from those described by Galfré & Milstein (Methods of Enzymology, Langone et al., eds., 73, pp. 3–46 [1981]).

In one preferred embodiment of the present invention, a hybridoma cell line is prepared as described above by fusing P3 X63-Ag86.5.3 mouse myeloma cell with an antibody-producing cell from the spleen of a BALB/c mouse which has been immunized with bovine La/SSB. This hybridoma cell line, designated as Lal, has been deposited with the American Type Culture Collection, Rockville, Md., and has been assigned accession number ATCC No. HB 8609. This deposit is available to the public upon the grant of a patent to the assignee. However, it should be understood that the availability of a deposit does not constitute a license to practice the invention in derogation of patent rights granted by governmental action.

Preferably, the antibody-producing hybridomas of the present invention are propagated in either of two ways. Hybridomas may be propagated in vivo by injecting a sample of the hybridoma into a histocompatible animal of the same species as the myeloma cell and the immunized animal described above. The animal so injected develops tumors which secrete specific monoclonal antibodies identical to those produced by the injected hybridoma. The monoclonal antibodies thus secreted collect in especially high concentrations in the serum and ascites fluid of the animal. Monoclonal antibodies against the selected autoimmune RNA protein may be recovered by extracting samples of these body fluids. Alternatively, selected hybridomas may be propagated in vitro in laboratory culture vessels from which the monoclonal antibodies against the selected autoimmune RNA protein can be harvested by decantation, filtration or centrifugation. This spent culture medium can then be used to purify the antibodies by established methods.

Preparation of Immunologically Active Fragments of Monoclonal Antibodies

When the monoclonal antibodies of the present invention are to be used in assaying methods, such as those involved in diagostic and screening techniques, it is frequently desirable to use only an immunologically active fragment of the monoclonal antibody—that is an antibody fragment which binds to the antigen under study. Use of such immunologically active fragments reduces unwanted sample interactions and minimizes unwanted background in assay results.

Immunologically active fragments of the monoclonal antibodies of the present invention may be prepared by digestion of the monoclonal antibodies with an enzyme, such as pepsin. A particularly preferred fragment of the monoclonal antibodies of the present invention is the F(ab')$_2$ fragment which is preferably prepared by pepsin digestion of purified immunoglobulin obtained from hybridoma-induced ascites fluid prepared as described above. Digestion is preferably followed by gel filtration.

When methods involving the use of monoclonal antibodies are described in this disclosure, it should be understood that immunologically active fragments of these monoclonal bodies may be equivalently and interchangeably substituted for the monoclonal antibodies in these methods.

Detection of Antibodies Against the Selected Autoimmune RNA Protein in a Biological Sample In accordance with the present invention, monoclonal antibodies produced as described above may be used to detect the presence in a biological sample of antibodies against a selected autoimmune RNA protein. The antibody detection method of the present invention is preferably practiced by use of monoclonal antibodies which are disposed in a reaction zone, which preferably comprises a protein-adsorbing surface such as that provided by a solid phase support such as a microtiter polystyrene plate, polystyrene tube or Sepharose beads. The monoclonal antibodies are preferably coated on the surface of the reaction zone, and held thereto in a fixed position. The coating step preferably is accomplished by incubating the monoclonal antibodies on the reaction zone surface for between about 2 and about 20 hours at between about 1° C. and about 24° C., higher temperatures being required for shorter incubation periods. More preferably, the monoclonal antibodies are incubated on the plates for about 16 hours (overnight) at about 4° C.

The unbound components from the monoclonal antibody containing medium preferably are removed next from the reaction zone. This removal is carried out so as to leave undisturbed the monoclonal antibodies which have been adsorbed on the surface of the reaction zone. This removal preferably is carried out by washing the reaction zone one or more times, preferably two times with an eluent to which the monoclonal antibodies are substantially inert. A preferred eluent is PBS-Tween, which is a preparation most preferably comprising 0.02M phosphate, 150 mM NaCl, 0.05% Tween (v/v) and 0.002% NaN$_3$(w/v) at a pH between about 7.0 and 7.4.

The monoclonal antibodies disposed in the reaction zone are treated with an animal extract which contains the selected autoimmune RNA protein in an amount in stoichiometric excess of the quantity of monoclonal antibodies disposed in the reaction zone. The extract preferably is obtained from the animal spleen or thymus. Preferably the extract is from the same animal species as the selected autoimmune RNA protein used to generate the antibody-producing cells which were fused to form the hybridoma which generated the monoclonal antibodies. Thus, if bovine La/SSB was used to generate the antibody-producing cells used in the hybridoma, then the animal extract should preferably be bovine as well. It should be understood that the animal extract need not be characterized by any particular degree of protein purity, as long as an excess of the selected protein is present.

The contacting of the monoclonal antibodies with the animal extract is carried out under conditions permitting RNA protein-antibody binding between the selected autoimmune RNA protein in the extract and antibodies disposed in the reaction zone. The contacting step preferably is carried out by incubating the extract in the reaction zone. Preferably, the extract is incubated for a period of between about 2 hours and about 18 hours, at a temperature of between about 1° C. and about 24° C., higher temperatures being required for shorter incubation periods. Most preferably, the extract is incubated for about 16 hours at about 4° C. The contacting step results in binding of the excess autoimmune RNA protein to a substantial number of the monoclonal antibodies disposed in the reaction zone, resulting in formation of a reactive substrate in the reaction zone. This reactive substrate comprises a reactive source of autoimmune RNA protein, which is bound to the monoclonal antibodies, which in turn preferably have been adsorbed onto the surface of the reaction zone as described previously.

After the reactive substrate is formed, unbound components from the extract are next preferably removed from the reaction zone. This removal is preferably carried out so as to retain the reactive substrate in a substantially intact condition in the reaction zone. This removal of unbound extract components is preferably carried out by washing the reaction zone one or more times, preferably two times, with an eluent to which the reactive substrate is substantially inert. A preferred eluent is PBS-Tween.

After the unbound extract components have been removed from the reaction zone, the reactive substrate is next contacted with a biological sample in which the presence of antibodies to the selected autoimmune RNA protein, if any, is to be detected. When the method of the present invention is used to detect the presence of antibodies in an animal, such as a human, the biological sample preferably comprises an animal fluid in which the antibodies of interest are known or suspected to exist. In such an instance, the biological sample will most preferably comprise animal serum.

The biological sample is contacted with the reactive substrate under conditions permitting antibody-RNA protein binding between antibodies to the selected autoimmune RNA protein, if any, in the sample and the autoimmune RNA protein in the reactive substrate. The contacting step preferably is carried out by incubating the sample in the reaction zone for between about 2 hours and about 18 hours, at a temperature of between about 1° C. and about 24° C. Shorter incubation periods require higher temperatures. More preferably the sample is incubated in the reaction zone for about 16 hours at about 4° C. or 2 hours at 24° C. (room temperature). The contacting step results in binding of antibodies to the selected autoimmune RNA protein, if any, in the sample to the autoimmune RNA protein in the reactive substrate.

After the sample contacting step is completed, the presence of antibodies to the selected autoimmune RNA protein in the sample, if any, is determined by asaying for antibody-RNA protein reaction occurring in the reaction zone after the sample is contacted therewith. By comparing the results of such a sample assay with the results of the same assay conducted on an antibody standard, the presence of antibodies to the selected autoimmune RNA protein may be both detected and quantified.

The assaying step may be carried out by any suitable procedure for detecting the occurrence of antibody-RNA protein reaction, such as radioimmunoassay or immunofluorescence assay. Most preferably, however, the assaying step is carried out by an enzyme-linked immunoabsorbent assay (ELISA).

Once the sample contacting step is complete, the ELISA is preferably carried out by removing unbound sample components from the reaction zone, so as to retain the reactive substrate and any sample antibodies bound thereto in a substantially intact condition in the reaction zone. This removal of unbound sample components is preferably carried out by washing the reaction zone one or more times, preferably four times, with an eluent to which the reactive substrate and any sample antibodies bound thereto are substantially inert. A preferred eluent is PBS-Tween.

After unbound sample components have been removed from the reaction zone, the reaction zone next is contacted with an enzyme-labelled immunological conjugate to the antibody to be detected, in an amount in stoichiometric excess relationship to the amount of antibodies to be detected. The selection of an appropriate immunological conjugate will depend on the origin of the biological sample in which antibodies are to be detected. Preferably, the conjugate comprises an enzyme conjugated to an immunoglobulin that will react (bind) with antibodies in the biological sample under study. When the biological sample is of human origin, the immunological conjugate preferably comprises goat anti-human immunoglobulin.

The immunological conjugate used in the preferred assay method utilizes an enzyme, such as alkaline phosphatase or peroxidase, which is capable of degrading a reagent by a degradation process which is accompanied by a perceptible color change. Suitable degradable reagents include paranitrophenolphosphate when the selected enzyme is alkaline phosphatase, and o-phenylenediamine with hydrogen peroxide when the selected enzyme is peroxidase. It should be noted that where the enzyme utilized in the conjugate is peroxidase, the eluent used to wash the reaction zone, as described above, should not contain azide.

The contacting of the immunological conjugate is carried out under conditions permitting binding between sample antibodies bound to the reactive substrate and conjugate immunoglobulin. This contacting step is preferably carried out by incubating the immunological conjugate in the reaction zone, preferably for a period of between about 1 hour and about 18 hours, at a temperature of between about 1° C. and about 24° C. More preferably the conjugate is incubated in the reaction zone for about 16 hours at about 4° C. This contact results in binding of the immunoglobulin in the conjugate to substantially all of the sample antibodies which have bound to the reactive substrate. Thus, the extent to which the conjugate binds to the reactive substrate is directly proportional to the quantity of antibodies against the selected autoimmune RNA protein contained in the sample under study.

Unbound components of the enzyme-linked immunological conjugate next are removed froth the reaction zone, so as to retain the sample antibodies and any immunological conjugate components bound thereto in substantially intact condition in the reaction zone. This removal of unbound immunological conjugate components preferably is carried out by washing the reaction zone one or more times, preferably four times, with an eluent to which the reactive substrate, any sample antibodies bound thereto, and any immunological conjugate components bound to sample antibodies, are substantially inert. A preferred eluent is PBS-Tween.

After the unbound immunological conjugate components have been removed from the reaction zone, the extent of conjugate binding to the sample antibodies is determined by contacting the degradable reagent with the immunological conjugate in the reaction zone. This contact permits a reaction between the enzyme of the conjugate and the degradable reagent which produces a perceptible color change in the reaction zone. The extent of color change caused by this reaction is preferably determined by measuring optical density of the reaction zone at the point of maximum absorbance. If it is necessary or desirable to delay the measurement of optical density, the reaction may be arrested by adding an appropriate counter reagent, such as 2 N NaOH, when the preferred absorbance is reached. By comparing the density measurement with the measurements obtained by conducting the same assay on antibody standards, the amount of antibodies in the sample can be quantified.

The above-described method of detecting antibodies to a selected autoimmune RNA protein may be used to screen a subject, such as a human or other animal, for an autoimmune disorder characterizable by elevated levels of such antibodies. Two such autoimmune disorders in humans are systemic lupus erythematosus and Sjögren's syndrome, in which many patients experience elevated levels of La/SSB, Ro/SSA, nRNP or Sm. By testing a serum sample of a subject in accordance with the above-described method of antibody detection, the presence of elevated levels of one or more of these antibodies in a subject can be detected, as required for diagnosis or screening for such autoimmune conditions.

The above-described antibody-detection method may be advantageously practiced with a kit for use in assaying for antibodies against a selected autoimmune RNA protein. The kit comprises a first medium, such as a container, comprising monoclonal antibodies to the selected autoimmune RNA protein, and most preferably comprising an ELISA plate to which monoclonal antibodies to the selected autoimmune RNA protein have been affixed. The kit further comprises a second medium, such as a container, comprising an animal extract in which the selected autoimmune RNA protein is present in stoichiometric excess relationship to the quantity of monoclonal antibodies in the first medium. The kit further comprises a third medium, such as a container, comprising an enzyme-immunoglobulin conjugate reactive with the biological sample.

The kit preferably further comprises a fourth medium, such as a container, comprising a reagent degradable by the enzyme in the third medium, by a degradation process accompanied by a perceptible color change. Preferably the kit further comprises a fifth medium, such as a container, comprising a counter-reagent for stopping the enzyme-reagent degradation reaction.

Detection of a Selected Autoimmune RNA Protein in a Biological Sample.

In accordance with the present invention, monoclonal antibodies produced as described above may be used to detect the presence in a biological sample of selected autoimmune RNA protein. The protein detection method of the present invention is preferably practiced by use of monoclonal antibodies which are disposed in a reaction zone, which preferably comprises a protein-adsorbing surface such as that provided by a solid phase support such as a microtiter polystyrene plate, polystyrene tube or Sepharose beads. The monoclonal antibodies preferably are coated on the surface of the reaction zone and adsorptively held thereto in a fixed position. The coating of the monoclonal antibodies on the surface of the reaction zone preferably is carried out by incubating the monoclonal antibodies on the solid phase support at between about 1° C. and about 24° C. for between about 2 hours and about 18 hours. More preferably, the monoclonal antibodies are incubated in the reaction zone at 4° C. for about 16 hours. The coating step results in the formation of a reactive substrate in the reaction zone which substrate preferably is fixed on the reaction zone surface.

The monoclonal antibodies which are not fixed on the surface of the reaction zone are removed from the reaction zone. The removal of the monoclonal antibodies not fixed on the surface of the reaction zone preferably is carried out by washing the reaction zone one or more times, preferably three times, with an eluent to which the monoclonal antibody coated surface of the reaction zone is substantially inert. A preferred eluent is PBS-Tween.

After the removal of the monoclonal antibodies which were not fixed on the reaction zone surface, the reactive substrate is contacted with a biological sample in which the presence of selected autoimmune RNA protein, if any, is to be detected. When the method of the present invention is used to detect the presence of RNA protein in an animal, such as a human, the biological sample preferably comprises an extract of animal tissue or animal fluid in which the protein of interest is known or suspected to exist. The method may also be adapted to permit detection of autoimmune RNA proteins produced by bacteria and other lower organisms governed by recombinant DNA technology.

The biological sample is contacted with the reaction substrate under conditions permitting antibody-RNA protein binding between the monoclonal antibodies as the reactive substrate and the selected autoimmune RNA protein, if any, in the biological sample. The contacting step preferably is carried out by incubating the sample in the reaction zone for between about 1 hour and about 18 hours, at a temperature of between about 1° C. and 24° C. More preferably, the sample is incubated in the reaction zone for about 16 hours at about 4° C. The step results in the binding of monoclonal antibodies in the reactive substrate to the selected autoimmune RNA protein, if any, in the sample.

After the sample contacting step is completed, the presence of selected autoimmune RNA protein in the sample, if any, is determined by assaying for antibody-RNA protein reaction occurring in the reaction zone after the sample is contacted therewith. By comparing the results of such a sample assay with the results of the same assay conducted on a selected autoimmune RNA protein standard, the presence of the selected autoimmune RNA protein may be both detected and quantified.

The assaying step may be carried out by any suitable procedure for detecting the occurrence of antibody-RNA protein reaction, such as radioimmunoassay or immunofluorescence assay. Most preferably, however, the assay step is carried out by enzyme-linked immunoabsorbent assay (ELISA), by the same procedure described previously with reference to the detection of antibodies in a biological sample.

The above-described method of detecting a selected autoimmune RNA protein may be used in the study of diseases and disorders which involve the presence of such proteins. This protein detection method may be practiced with a kit for use in assaying for a selected autoimmune RNA protein. Preferably, the kit comprises a first medium, such as a container, comprising monoclonal antibodies to the selected autoimmune RNA protein, and, most preferably, an ELISA plate coated with monoclonal antibodies to the selected autoimmune RNA protein, and a second medium, such as a container comprising an enzyme-immunoglobulin conjugate reactive with the biological sample. The kit preferably further comprises a third medium, such as a container, comprising a reagent degradable by the enzyme in the second medium, by a degradation process accompanied by a perceptible color change. Preferably, the kit further comprises a fourth medium, such as a container, comprising a counter-regent for stopping the enzyme-reagent degradation reaction.

The following examples illustrate the practice of the methods of the present invention and the preparation and use of the compositions of the present invention.

EXAMPLE I

Purification of La/SSB

An affinity chromatography method was used to purify the La/SSB protein as described by Harley et al., (J. Rheumatol. 11, pp. 309-14 [1984]) and Akizuki et al. (J. Immunol. 119, pp. 932-38 [1977]). Calf thymus, bovine spleen and human spleen were extracted with an equal volume (wt:vol) of 2 mM dithiothreitol in phosphate buffered saline (PBS). The 60-80% (saturated) ammonium sulfate fraction was dialyzed against PBS and applied to an affinity column onto which was bound the IgG fraction of an SLE patient whose serum was known to have a particularly high concentration of anti-La/SSB IgG. The affinity column was made by coupling the purified IgG fraction from an SLE patient with anti-La/SSB precipitin to CNBr activated Sepharose 4B (Pharmacia Fine Chemicals, Piscataway, N.J.) by established methodology (Axen et al., Nature 214, pp. 1302-04 [1967]). La/SSB was eluted with 3M $MgCl_2$ at pH 7.0. The eluate was dialyzed and passed through a gel filtration column (Bio-Gel A-0.5 m, Bio-Rad Laboratories, Richmond, Calif.) in a tris buffer at pH 7.2.

The La/SSB fractions were analyzed for contamination by: (1) sodium dodecylsulfate (SDS) polyacrylamide gel electrophoresis (Laemmli, Nature 227, pp. 680-85 [1970]) using a silver stain (Merril et al., Science 211, pp. 1437-38 [1981]); (2) the Western blot technique (Towbin et al., Proc. Nat'l. Acad. Sci. USA 76, pp. 4350-54 [1979] and Burnette, Anal. Biochem. 112, pp. 195-203 [1981]); and, (3) an anti-La/SSB ELISA (Harley et al., J. Rheumatol., 11, pp. 309-14 [1984]).

Monospecific anti-Ro/SSA and anti-human immunoglobulin affinity column procedures were used to eliminate any contamination of the preparation with Ro/SSA and/or immunoglobulin. The fractions displaying antigenic activity were pooled, concentrated and stored at $-70°$ C.

EXAMPLE II

Immunization of a Mouse With Purified La/SSB

To obtain cells capable of producing antibodies to bovine La/SSB, a Balb/c mouse was immunized with purified homogenous bovine La/SSB that was obtained as described in Example I. On day 1 the mouse received a subcutaneous injection containing 50 µg purified bovine La/SSB suspended in 200 µl of 0.02M Tris and 150 mM NaCl at pH 7.4 (TBS) in combination with 200 µl of Freund's Complete Adjuvant. On day 14 the mouse was boosted by an intraperitoneal injection of 10 µg purified bovine La/SSB suspended in 100 µl of TBS and 200 µl of Freund's Incomplete Adjuvant. Over the next four months the mouse was boosted seven times by intraperitoneal injections of 10 to 100 µg La/SSB, each dosage being suspended in between about 50 µl and about 200 µl TBS and administered without adjuvant. On each of the three days before spleen cells were removed, the mouse received booster injections of La/SSB. The first two of the boosts were administered intraperitoneally and the final boost was administered to the tail vein.

EXAMPLE III

Production and Cloning of Hydbridomas Producing Monoclonal Antibodies to La/SSB

Spleen cells of the mouse immunized according to the procedure in Example II were extracted by conventional methods. Murine myeloma fusion partner cells P3 X63-Ag86.5.3 were selected for fusion with the spleen cells.

The fusion of the spleen cells with the myeloma cells, the selective culturing of the resulting hybridoma cells and the cloning of antibody-producing hybridomas were performed in accordance with the procedures described by Galfre and Milstein (Methods of Enzymology, Langone et al., eds., 73, pp. 3-46 [1981]). The myeloma cells were mixed with the spleen cells in a HAT medium. A polyethylene glycol (PEG) solution was added to the mixture to promote fusion. After fusion had occurred, the action of the PEG was arrested by adding additional HAT medium to the mixture.

The fused cells next were selectively cultured by plating them out onto 24-well polystyrene plates. The wells of the plate contained a mixture of HAT medium and fetal calf serum (FCS) which is selective for the growth of hybridoma cells formed by fusion of myeloma cells with antibody-producing cells.

The wells demonstrating hybridoma growth were screened for the presence of antibodies against La/SSB protein by an enzyme-linked immunoabsorbent assay using a peroxidase-anti-mouse immunoglobulin conjugate. The hybridomas which were positive for antibody production and which survived and grew in the wells were single-cell cloned by plating them out into a 96-well plate. The wells of the plate contained a HAT and FCS mixture. The FCS used was Hybrisure (Hazelton-Dutchland). The hybridomas were allowed to colonize.

After colonization of the hybridomas had occurred, the wells were screened to detect which of the hybridomas were producing antibodies against La/SSB. Screening of the hybridomas for antibody production was carried out by the enzyme-linked immunoabsorbent assay (ELISA) technique (also using a peroxidase-anti-mouse immunoglobulin conjugate) of Engvall and Perlman (Immunochemistry, 8, pp. 871-74 [1971]), which was modified as described by Harley et al. (J. Rheumatol., 11, pp. 309-14 [1984]). The ELISA utilized affinity-purified bovine La/SSB and identified five wells containing antibody-producing hybridomas.

EXAMPLE IV

Characterization of Monoclonal Antibodies by Species Specificity Testing

Supernatant from three of the five wells which contained the antibody-producing hybridomas prepared as described in Example III was used to test for species specificity. Testing was carried out by separately incubating La/SSB from various animal species with final samples of each supernatant. The optical density of the resulting fluid mixture was measured with a Microelisa Reader MR580 (Dynatech, Alexandria, Va.) as an assay for antibody-La/SSB reaction.

The results of the tests are summarized in Table I. These results indicate that the antibody-binding activity of each of the three supernatants, when used at the appropriate dilution, was inhibited by extracts containing human or rabbit La/SSB.

Each of the three supernatants were subjected to the Western blot technique to determine if reactivity was actually with the La/SSB moiety or with a minor contaminant in the bovine La/SSB tissue extracts. The results of these tests disclosed that each of the three supernatants bound only the larger of the La/SSB peptides.

Stable clones were produced from only two of the three antibody-producing hybridomas. Based on the observation that antibodies produced by both of these clones bound only to the larger bovine La/SSB peptide, it was concluded that the antibodies produced by the two clones were otherwise similarly reactive. One of these two clones, taken from the well designated Well No. 2 in Table I, was selected for further investigation. This cell line, designated Lal, has been deposited with the American Type Culture Collection, Rockville, Md., and has been assigned accession number ATCC No. HB 8609.

precipitating properties of human serum known to contain anti-La/SSB precipitin. The serum was prepared for testing by adding 10 to 50 μl of serum to 2.5 mg. preswollen protein A Sepharose (Pharmacia). The serum-treated protein then was incubated separately with cell extracts as described above with reference to Lal-treated protein. RNA was likewise extracted and autoradiographed from the incubated protein as de-

TABLE I

Inhibition of Hybridoma Supernatant Anti-La/SSB Binding Activity by La/SSB from Different Sources (Expressed in Optical Density Units)

| Hybridoma Supernatant: | None | crude Calf Thymus Extract | crude Human Spleen Extract | 10% Calf Thymus Extract | 20% Human Spleen Extract | 10% Rabbit Thymus Extract |
|---|---|---|---|---|---|---|
| Experiment 1 | | | | | | |
| Well No. 1 | 1.107 | 0.473 | 1.122 | 0.341 | 1.249 | 1.249 |
| Well No. 2 (Lal) | 1.101 | 0.954 | 1.245 | 0.548 | 1.395 | 1.322 |
| Well No. 3 | 1.139 | 0.978 | 1.241 | 0.636 | 1.379 | 1.284 |
| Experiment 2 | | | | | | |
| Well No. 1 [1:10]* | 0.723 | 0.161 | N.D.** | 0.033 | 0.680 | 0.692 |
| Well No. 2 (Lal) [1:4] | 1.154 | N.D. | N.D. | 0.207 | 1.166 | 1.199 |
| Well No. 3 [1:10] | 1.059 | 0.462 | N D. | 0.089 | 1.043 | 1.064 |

*Dilutions of hybridoma culture supernatants are expressed in ratio of number of parts of supernatant in the total number of parts of dilution.
**N.D.: Not determined.

EXAMPLE V

Characterization of Monoclonal Antibodies by RNA Immunoprecipitation

In the course of characterizing the monoclonal antibodies against La/SSB, the ability of these antibodies to precipitate RNA from various sources was investigated. This analysis of RNA immunoprecipitation was conducted in accordance with the procedures described in Lerner et al., Proc. Natl. Acad. Sci. USA 76, pp. 5495–99 [1979] and Mimori et al., J. Biol. Chem. 259, pp. 560–65 [1984]. These procedures were as follows.

Phosphorus 32-labelled cell extracts of MDBK (bovine) and HeLa (human) cell lines were separately preincubated with Pansorbin (Calbiochem. Behrin, La Jolla, Calif.) in 150 mM sodium chloride, 50 mM Tris-HCl and 0.05% Nonidet P-40 at pH 7.5. The preincubated bovine and human cull extracts thus produced were used to test the RNA-precipitating properties of Lal antibodies, as follows.

Lal antibodies were covalently bound to cynogen bromide-activated Sepharose 4B (Pharmacia), pursuant to the manufacturer's instructions, and were incubated with goat anti-mouse IgG which was bound to protein A Sepharose. The bound monoclonal antibodies were separately incubated with $10^6$ to $10^7$ cells from each of the preincubated bovine and human cell extracts described above. After incubation was complete, the Sepharose was washed repeatedly. Its protein was denatured in SDS and sodium acetate, and RNA was extracted with phenol:chloroform:isoamyl alcohol mixture formulated in a 50:50:1 ratio. The RNA species in the ethanol precipitate were separated by 7M urea, 10% polyacrylamide gel electrophoresis, and were autoradiographed.

The preincubated bovine and human cell extracts described above also were used to test the RNA-scribed above.

These studies revealed that Lal antibodies immunoprecipitated RNA only from the bovine cell extract, and not from the human cell extract. The human serum containing anti-La/SSB precipitin immunoprecipitated RNA from both the bovine cell extract and the human cell extract.

EXAMPLE VI

Characterization of Monoclonal Antibodies by Antinuclear Antibody Techniques The species specificity of Lal monoclonal antibodies was further investigated by an antinuclear antibody (ANA) technique. Tissue substrates from four different species, rabbit, mouse, bovine and human were used in determining the presence of antinuclear antibodies. The SIRC rabbit corneal epithelial line (ATCC-CCL60), the NCTC clone of the 929 mouse fibroblast line (ATCC-CCL1), and the MDBK bovine kidney line (ATCC-CCL22) were grown on slides in RPMI 1640 with 50 g/ml gentamycin, 5 mM glutamine and 10% fetal calf serum. Human HEp-2 slides were purchased from Breit Laboratories, Inc., West Sacramento, Calif.

Two different antibody-containing test preparations were used to treat the tissue slides described above. The treated slides then were analyzed for presence of antinuclear antibodies. Standard techniques were used for the ANA determination with these substrates using goat anti-human flouresceinated IgG (Breit) or goat anti-mouse fluoresceinated IgG (Sigma) as was appropriate for the source of antibody being studied.

The first test preparation was prepared from serum selected from an SLE patient. Each of the tissue substrates described above was reacted with the serum preparation, and each exhibited reactivity with substrates of tissue derived from all four species, namely human (HEp-2), bovine (MDBK), rabbit (SIRC) and mouse (NCTC 929).

The ANA reactivity of the human serum to substrates of each of the four species could be blocked by incubating the serum with 10 µg/ml bovine La/SSB.

The second test preparation was Lal hybridoma-induced ascites fluid. When treated with each of the tissue substrates described above, this preparation exhibited reactivity only with the bovine (MDBK) substrate. The results of these ANA studies are summarized in Table II.

The ANA reactivity of the Lal ascites fluid to the bovine substrate could be blocked by incubating the ascites fluid with 10 µg/ml bovine La/SSB.

TABLE II

Comparison of ANA Reactivity of SLE Serum and Lal-Induced Ascites Fluid To Various Animal Cell Lines (expressed in endpoint ANA titers)

| Anti-La/SSB Source | Tissue Substrate | | | |
|---|---|---|---|---|
| | Human (HEp-2) | Bovine (MDBK) | Rabbit (SIRC) | Mouse (NCTC 929) |
| Human SLE serum | 1:3200 | 1:3200 | 1:800 | 1:1600 |
| Lal-induced ascites fluid | <1:20 | 1:25,600 | <1:20 | <1:20 |

The reaction between Lal ascites fluid and the bovine substrate produced a nuclear ANA pattern which resembled that produced by the reaction between the bovine substrate and the human serum containing anti-La/SSB antibodies.

EXAMPLE VII

Preparation of Ascites Fluid, IqG Purification, and F(ab')$_2$ Fragment Preparation Ascites fluid was prepared by injecting pristine (Aldridge Chemical Company, Milwaukee, Wis.) primed Balb/c mice with stable cloned Lal producing cells. Purified IgG was prepared from ascites fluid by treating the fluid with DE-52 (Watman Inc., Clifton, N.J.) or Affi-Gel Blue (Bio-Rad) column chromatography as described by Catalano et al. (J. Clin. Invest. 60, pp. 313-22 [1977]) and Brack et al. (J. Immunol. Methods 53, pp. 313-19 [1982]). Immunologically active F(ab')$_2$ fragments of the monoclonal antibodies in the purified IgG were generated by pepsin digestion of the IgG followed by Sephadex G100 (Pharmacia) gel filtration as described by Campbell et al. (Methods in Immunology, 2nd ed., W. A. Benjamin, ed., New York, N.Y., pp. 224-34 [1970]).

EXAMPLE VIII

Detection of Antibodies Against La/SSB in a Biological Sample

In order to measure the presence of antibodies against La/SSB in a biological sample, the enzyme-linked immunoabsorent assay (ELISA) technique was modified to make use of Lal monoclonal antibodies. Microtiter plates were treated with a fluid medium containing an optimum of 10 g/ml of the purified Lal monoclonal antibodies. The fluid medium was allowed to remain on the plate for 16 hours (overnight) at 4° C. to allow the Lal antibodies to adhere to the surface of the plate. The unbound components are then removed and the plate is washed 2 times with PBS-Tween. The plate then was treated with a saturating concentration of La/SSB-containing bovine spleen extract from which Ro/SSA protein had been depleted by affinity chromatography. The spleen extract was incubated on the plate for 16 hours at 4° C. After washing the plate two times with PBS-Tween, a human serum sample, diluted to between about 1 part serum to about 100 to 10,000 parts diluent, was incubated on the plate for 16 hours at 4° C. The diluent used was PBS-Tween containing 0.1% bovine serum albumin. The plate was then washed again 4 times with PBS-Tween.

An enzyme conjugate of goat anti-human IgG and alkaline phosphatase (Sigma) was incubated on the plate for 16 hours at 40° C. A paranitrophenolphosphate substrate solution was applied to the plate, thereby causing a hydrolysis reaction to begin. The optical density of the plate was measured at 405 mm. By comparing this figure with optical densities produced by following the same procedure with standard quantities of antibodies, the presence of antibodies in the sample could be determined and the amount of such antibodies could be quantified.

The sensitivity of the above procedure was improved by using F(ab')$_2$ fragments prepared according to Example VII in lieu of the IgG Lal monoclonal antibodies.

EXAMPLE IX

Clinical Testing

Serum samples from 25 individuals, divided into groups according to medical diagnosis and presence or absence of Ro/SSA and La/SSB precipitins, were assayed by an enzyme-linked immunoabsorbent assay (ELISA) using purified La/SSB and by an ELISA using Lal antibodies prepared in accordance with the present invention. Each assay was performed on each sample numerous times. The results expressed in Table III below represent an average of selected multiple determinations from such assays.

Serum samples from ten normal individuals which tested negative for Ro/SSA and La/SSB by a precipitin test were assayed for antibodies against La/SSB first by an ELISA using purified bovine La/SSB prepared in accordance with Example I and then by an ELISA using Lal monoclonal antibodies in accordance with Example VII. The results of the two ELISAs show that all these samples displayed a lower reactivity in the ELISA using the Lal antibodies as shown in Section A of Table III.

Table III, Section B, summarizes the results of the two ELISAs on the serum samples from three patients diagnosed as having SS or SLE who tested positive for Ro/SSA and La/SSB by the precipitin test. These samples showed a response in an ELISA using the Lal antibodies which was comparable to the response obtained from an ELISA using purified La/SSB.

As is shown in Table III, Section C, the serum samples from five SLE or SS patients who tested positive for Ro/SSA and negative for La/SSB under the precipitin test and negative for La/SSB under the ELISA using purified La/SSB, only one did not have substantial reactivity above background in the ELISA using the Lal antibodies.

Three normal individuals who tested negative by precipitation for La/SSB and Ro/SSA but who tested positive under an anti-La/SSB ELISA using purified La/SSB, were shown by the Lal ELISA using the Lal antibodies to have substantial levels of anti-La/SSB antibodies in their serum although these levels were significantly lower than those found by the ELISA using purified La/SSB. These results are shown in Section D of Table III.

Finally, as shown by Section E of Table III, a group of three SLE or SS patients who had tested positive for Ro/SSA and negative for La/SSB by precipitation and positive for La/SSB by an ELISA using purified La/SSB, tested positive for anti-La/SSB antibodies under the ELISA using Lal antibodies but showed significantly higher antibody levels when the ELISA used Lal antibodies rather than purified La/SSB.

TABLE III

Results of Assays for Anti La/SSB Antibodies in Normal and SLE/SS[1] Patients[2]

| DONOR NO. | SS or SLE | Precipitin Ro/SSA | Precipitin La/SSB | ELISA using purified La/SSB | ELISA using Lal antibodies |
|---|---|---|---|---|---|
| | | | Section A | | |
| 1 | no | — | — | 224 | 52 |
| 2 | no | — | — | 175 | 29 |
| 3 | no | — | — | 69 | 32 |
| 4 | no | — | — | 443 | 42 |
| 5 | no | — | — | 79 | 23 |
| 6 | no | — | — | 683 | 26 |
| 7 | no | — | — | 29 | 120 |
| 8 | no | — | — | 845 | 32 |
| 9 | no | — | — | 30 | 33 |
| 10 | no | — | — | 444 | 112 |
| | | | Section B | | |
| 11 | yes | + | + | 13,800,000 | 20,000,000 |
| 12 | yes | + | + | 13,500,000 | 22,900,000 |
| 13 | yes | + | + | 8,300,000 | 14,300,000 |
| 14 | yes | + | + | 6,900,000 | 4,830,000 |
| | | | Section C | | |
| 15 | yes | + | — | 158 | 237 |
| 16 | yes | + | — | 409 | 912 |
| 17 | yes | + | — | 120 | 20,400 |
| 18 | yes | + | — | 640 | 3,020 |
| 19 | yes | + | — | 120 | 1,260 |
| | | | Section D | | |
| 20 | no | — | — | 7,200 | 195 |
| 21 | no | — | — | 22,000 | 3,160 |
| 22 | no | — | — | 21,000 | 1,820 |
| | | | Section E | | |
| 23 | yes | + | — | 29,500 | 155,000 |
| 24 | yes | + | — | 40,000 | 756,000 |
| 25 | yes | + | — | 45,000 | 151,000 |

[1] SS=Sjögren's Syndrome; SLE=systemic lupus erthematosus. [2] Results are expressed in units, one unit being the measure of reactivity present in $10^{-7}$ of a standard La/SSB precipitin-positive serum sample.

Changes may be made in the nature, composition, operation and arrangement of the various elements, steps and procedures described herein without departing from the spirit and scope of the invention as defined in the following claims.

What is claimed is:

1. A method for producing monoclonal antibodies against an autoimmune RNA protein selected from the group consisting of Ro/SSA and La/SSB, comprising:
    propagating a hybridoma which is characterized as having been generated by fusing a myeloma cell with a cell capable of producing antibodies against the selected autoimmune RNA protein; and
    harvesting the monoclonal antibodies produced by the hybridoma.

2. A method of claim 1 in which the autoimmune RNA protein is La/SSB.

3. The method of claim 2 in which the autoimmune RNA protein is bovine La/SSB.

4. The method of claim 1 in which the myeloma cell is murine.

5. The method of claim 1 in which the autoimmune RNA protein is bovine La/SSB and in which the myeloma cell is murine.

6. The method of claim 1 in which the autoimmune RNA protein is Ro/SSA from a selected one of humans and bovines.

7. The method of claim 1 in which the cell capable of producing antibodies against the autoimmune RNA protein is characterized as having been prepared by:
    immunizing an immunoresponsive animal of a first species with an autoimmune RNA protein from a second and different animal species; and
    recovering cells capable of producing antibodies against the autoimmune RNA protein from the immunized animal.

8. The method of claim 7 in which the autoimmune RNA protein is Ro/SSA from a selected one of humans and bovines.

9. The method of claim 7 in which the first species is murine and the second species is bovine.

10. The method of claim 7 in which the autoimmune RNA protein is La/SSB.

11. The method of claim 10 in which the autoimmune RNA protein is bovine La/SSB.

12. The method of claim 7 in which the myeloma cell is murine.

13. The method of claim 7 in which the autoimmune RNA protein is bovine La/SSB and in which the fused cells are each murine.

14. A method for producing monoclonal antibodies against an autoimmune RNA protein, comprising:
    propagating a hybridoma which is characterized as having been generated by fusing a myeloma cell with a cell capable of producing antibodies against the autoimmune RNA protein, which cell is characterized as having been prepared by:

immunizing an immunoresponsive animal of a first murine species with an autoimmune RNA protein from a second and different non-murine animal species; and recovering a cell capable of producing antibodies against the autoimmune RNA protein from the immunized animal; and harvesting the monoclonal antibodies produced by the hybridoma.

15. The method of claim 14 in which the first species is murine and the second species is bovine.

16. The method of claim 14 in which the autoimmune RNA protein is Ro/SSA.

17. The method of claim 16 in which the autoimmune RNA protein is bovine Ro/SSA.

18. The method of claim 14 in which the myeloma cell is murine.

19. The method of claim 14 in which the autoimmune RNA protein is bovine Ro/SSA and in which the fused cells are each murine.

20. A method for producing a continuous cell line capable of producing antibodies against a selected autoimmune RNA protein comprising:

immunizing an immunoresponsive animal of a first species with the selected autoimmune RNA protein from a second and different animal species;

recovering a cell capable of producing antibodies against the selected autoimmune RNA protein from the immunized animal; and fusing a recovered cell capable of forming antibodies against the selected autoimmune RNA protein with a myeloma to produce a continuous cell line.

21. The method of claim 20 in which the first species is murine and the second species is bovine.

22. The method of claim 20 in which the selected autoimmune RNA protein is Ro/SSA.

23. The method of claim 20 in which the selected autoimmune RNA protein is La/SSB.

24. The method of claim 20 in which the myeloma cell line is murine.

25. A method for producing a cell capable of producing antibodies against a selected autoimmune RNA protein, comprising:

immunizing an immunoresponsive animal of a first species with the selected autoimmune RNA protein from a second and different animal species; and recovering a cell capable of producing antibodies against the selected autoimmune RNA protein from the immunized animal.

26. The method of claim 25 in which the first species is murine and the second species is bovine.

27. The method of claim 25 in which the selected autoimmune RNA protein is Ro/SSA.

28. The method of claim 25 in which the selected autoimmune RNA protein is La/SSB.

* * * * *

UNITED STATES PATENT AND TRADEMARK OFFICE
CERTIFICATE OF CORRECTION

PATENT NO. : 5,264,351

DATED : November 23, 1993

INVENTOR(S) : John B. Harley

It is certified that error appears in the above-identified patent and that said Letters Patent is hereby corrected as shown below:

Title Page, in the Abstract, line 11, please delete "Siögren's", and substitute therefore --Sjögren's--.

Column 8, line 31, please delete "froth", and substitute therefore --from--.

Column 15, lines 57 and 58, please delete "immunoabsorent", and substitute therefore --immunoabsorbent--.

Column 16, line 15, please delete "405 mm", and substitute therefore --405 mM--.

Column 17, lined 44 and 45, please delete "erthematosus", and substitute therefore --ery-thematosus--.

Signed and Sealed this

Twenty-third Day of August, 1994

Attest:

BRUCE LEHMAN

Attesting Officer

Commissioner of Patents and Trademarks